United States Patent [19]

Thornton et al.

[11] 4,437,987

[45] Mar. 20, 1984

[54] ANAEROBIC DIGESTER GAS COLLECTION AND STORAGE SYSTEMS

[76] Inventors: Marvin L. Thornton, 509 SE. Fourth, Ankeny, Iowa 50021; Arthur J. Boyt, Jr., 4602 Kingman, Des Moines, Iowa 50311

[21] Appl. No.: 394,405

[22] Filed: Jul. 1, 1982

[51] Int. Cl.³ .................... C02F 11/04; C12M 1/02
[52] U.S. Cl. .................... 210/137; 210/180; 210/218; 210/DIG. 9; 435/316; 220/85 A; 220/85 B; 220/426
[58] Field of Search ............ 210/603, 608, 178, 218, 210/DIG. 9, 180, 741, 137; 220/85 B, 85 A, 227, 426, 461, 216; 48/197 A; 435/316, 167; 422/184

[56] References Cited

U.S. PATENT DOCUMENTS

| | | | |
|---|---|---|---|
| 3,122,985 | 3/1964 | Osborne | 220/85 B |
| 3,981,803 | 9/1976 | Coulthard | 210/180 |
| 4,060,175 | 11/1977 | Rysgaard, Sr. | 220/85 B |
| 4,166,835 | 9/1979 | Anderson | 210/DIG. 9 |
| 4,256,837 | 3/1981 | Fluri et al. | 210/DIG. 9 |
| 4,375,784 | 3/1983 | Kalnins | 220/85 B |

*Primary Examiner*—Benoît Castel
*Attorney, Agent, or Firm*—James D. Birkenholz

[57] ABSTRACT

In an anaerobic sludge digestion tank system having walls communicating with a floor forming a storage container for the sludge and a fixed outer cover overlaying the storage container having a center stack communicating with the storage container, a flexible gas membrane is provided extending between the wall and the center stack over and above the storage container and a pressurizing membrane extends over the top of the gas membrane between the gas membrane and the cover and between the wall and center stack. The two membranes are sealingly attached to the top of the wall at their bottom portion and the center stack at their upper portion and form an inner pressurizing chamber.

An air injection system is provided for injection of air under pressure between the gas membrane and the pressure membrane into the inner chamber thus forcing the inner chamber to expand via the downward movement of the gas membrane. The controllable expansion of the inner chamber maintains and regulates the pressure of the gas produced by the anaerobic process that collects between the top of the sludge mixture and the bottom of the gas membrane.

6 Claims, 6 Drawing Figures

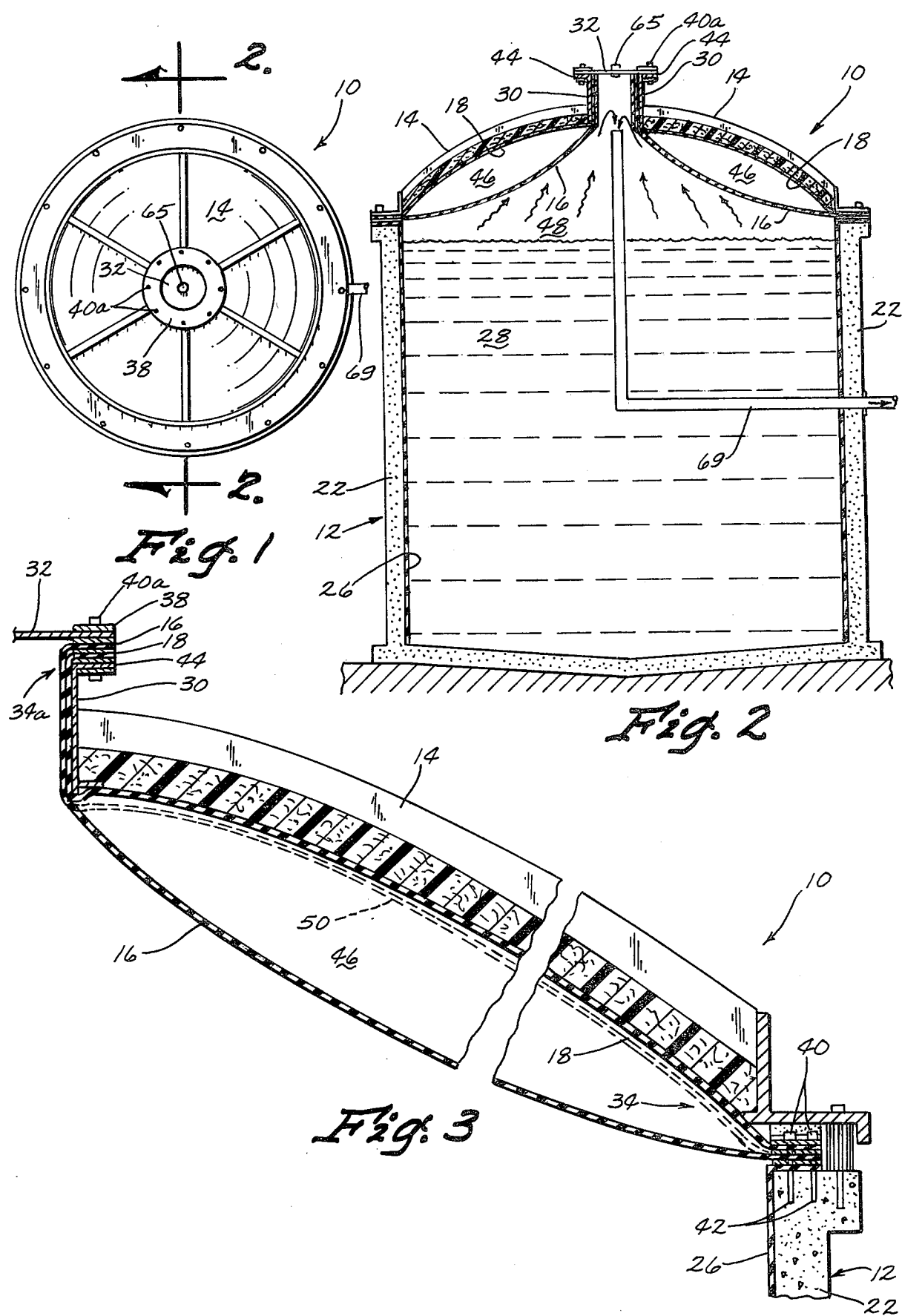

ANAEROBIC DIGESTER GAS COLLECTION AND STORAGE SYSTEMS

BACKGROUND OF THE INVENTION

1. Field of the Invention

The present invention relates generally to equipment for the treatment of waste material and more particularly to anaerobic sludge digestion tank equipment utilizing a double membrane to maintain constant pressure in a variable volume region housing the gas produced during the anaerobic process.

2. Background of the Invention

The use of digestive tanks utilizing anaerobic treatment of waste water sludge is well known and practiced in the art. During the anaerobic process, gases, typically methane and carbon dioxide, are given off and collected to be used as the fuel for heating the sludge mixture. Many of the systems employ a floating gas holder positioned above the sludge which collects the gas and provides a controllable downward force on the gas, thus resulting in the gas being pressurized and immediately useable in the sludge heating equipment. The tank facilities must meet environmental limitations concerning the discharge of gases into the atmosphere and careful monitoring and control of the gases produced during the anaerobic process is essential since the gases frequently are explosive when intermixed with ambient atmospheric air. The floating gas holder while in theory is workable, is subject to corrosion and freezing, thus limiting its movement as well as tipping and gas leakages, all of which substantially interfere with its effective operation to properly control the gas within the tank. The optimum digestive tank would employ a system which would be capable of adapting to a changing volume of sludge mixture within the tank while still providing a constant pressure reservoir for the gas produced. Further, it is desirable that the system be capable of controlling the gases produced and hold them in a constant pressure environment while functioning without an external energy source over a reasonable period of time since the anaerobic process is not dependent upon external energy and would continue during periods of power outages and control of the system for the above stated reasons must be maintained.

SUMMARY OF THE INVENTION

In an anaerobic sludge digestion tank having a flexible gas membrane extending over the sludge mixture and between the outside wall of the tank and the center stack of the cover. A pressurizing membrane extends over the gas membrane and between the wall and the center stack. Each of the membranes are sealingly attached at the wall and center stack and form an inner pressurizing chamber between their communicating surfaces. An air injection system injects air under pressure into the inner chamber resulting in expansion of the inner chamber and a downward movement of the gas membrane to maintain and regulate the pressure of the gas produced by the anaerobic process existing in the area between the top of the sludge and the bottom of the gas membrane.

BRIEF DESCRIPTION OF THE DRAWINGS

FIG. 1 is a top perspective view of the anaerobic digester gas collection and storage system;

FIG. 2 is a side cross-sectional taken along lines 2—2 of FIG. 1;

FIG. 3 is a partial side cross-sectional view of the upper portion of the digester tank illustrating the tank cover and gas and pressure membranes;

DESCRIPTION OF THE PREFERRED EMBODIMENT

Figure 4:
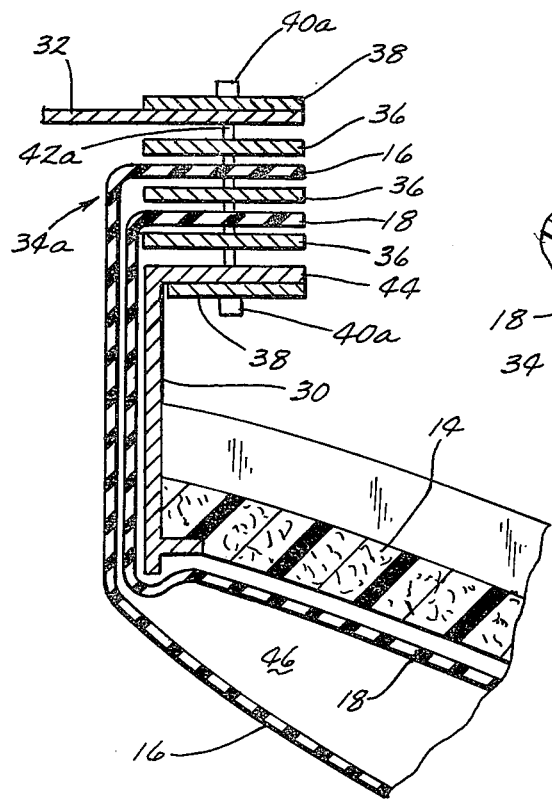
FIG. 4 is a partial cross-sectional view of the stack, cover and juncture membranes.

Referring now to the drawings wherein like reference numerals designate identical or corresponding parts throughout the several views, the anaerobic digester tank is indicated generally at 10 in FIG. 1.

Figure 5:
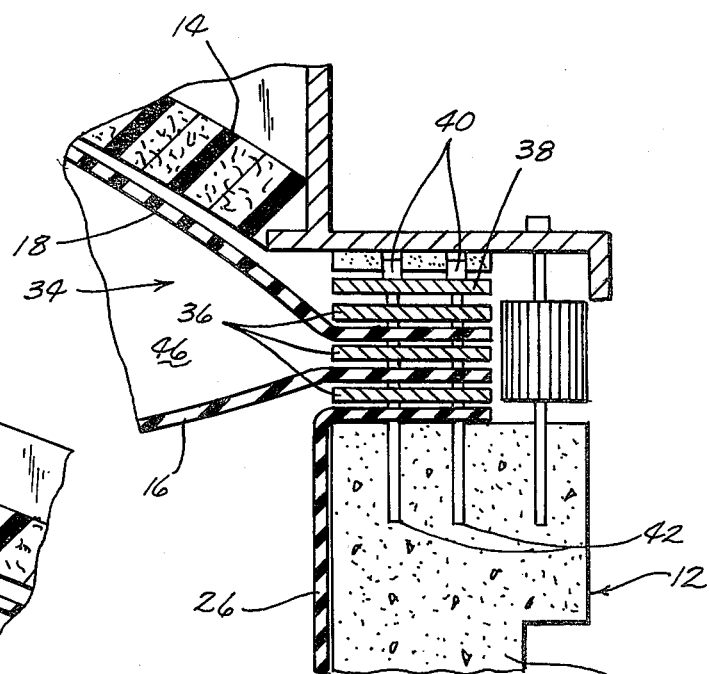
FIG. 5 is a partial cross-sectional view of the juncture of the wall, membranes and cover.
Figure 6:
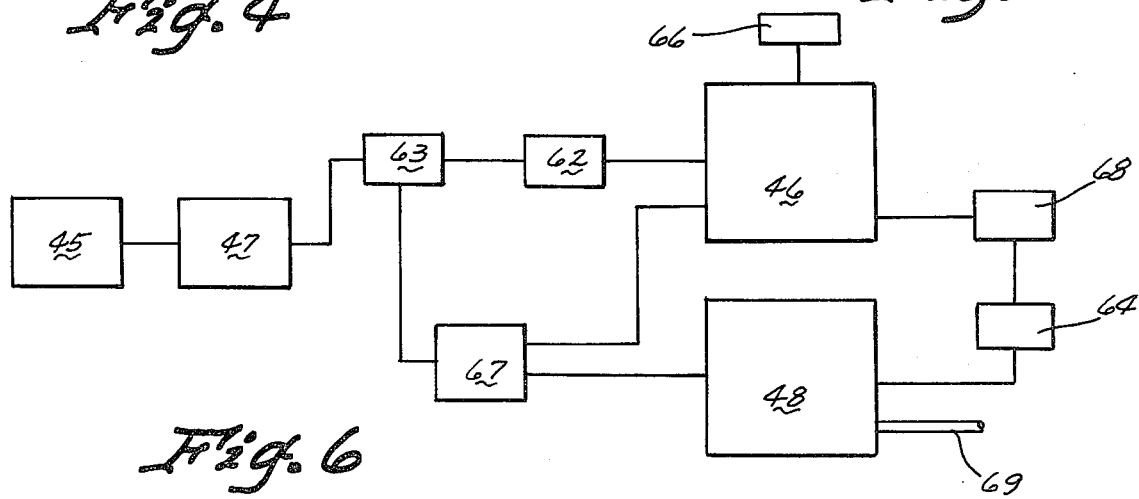
FIG. 6 is a block diagram of the air injection system.

Generally, the digester 10 (FIGS. 1, 2, 5 and 6) includes a storage container 12 having a rigid outer cover 14, a gas membrane 16 and pressurizing membrane 18 and an air injection system.

Specifically, the storage container 12 (FIGS. 1–5) includes a wall 22 and floor 24 with a container liner 26 around the inside surface of the wall 22 and floor 24. The storage container 12 is adapted to hold a variable volume of liquid waste sludge 28. The cover 14 is typically convex in configuration and rigidly secured to the upper portion of the wall 22 by conventional means and includes a center stack 30 extending through the apex of the cover 14. The stack 30 communicates with the interior of the storage container 12 and is sealed by a cover plate 32 which is removable to allow access to the interior region of the container 12.

The gas membrane 16 (FIGS. 1–5) is constructed of flexible material which is chemically inert and impermeable to the sludge 28 and by-products of the anaerobic breakdown of the sludge 28. The membrane 16 extends between the wall 22 and the center stack 30 in an annular configuration over and above the top level of the sludge 28. The membrane 16 is supported and secured to the top portion of the wall 22 by a sealing unit 34 which includes a series of compressionable gaskets 36 placed between the liner 26, the membranes 16 and 18 and a plate 38 which draws the material together by tightening nuts 40 on a series of threaded rods 42 immersed in the top portion of the wall 22. The upper portion of the membrane 16 is likewise secured by a sealing unit 34a to the stack 30 by compression gaskets 36 placed between the upper lip 44 of the stack 30 and the membrane 16, membrane 18 and plate 32 by compressing the material together by tightening the nuts 40a on the threaded rods 42a. The pressure membrane 18 constructed of flexible material extends over the top of the gas membrane 16 and underneath the cover 14 and between the wall 22 and the center stack 30. The membrane 18 is sealingly fastened to the wall 22 and stack 30 by the respective sealing units 34 and 34a. The space between the gas membrane 16 and pressure membrane 18 defines an inner pressurizing chamber 46.

A spacer is provided to allow the cover to be tightened against the wall 22 without pulling the outside rim of the cover 14 against the nuts and rods 40 and 42 respectively.

The gas produced by the anaerobic process is removed from the reservoir 48 by pipe 69 which extends above the sludge mixture 28. The gas being generated typically is burnable and is used to heat the sludge mixture in order to increase the anaerobic rate of decomposition. If the gas within the reservoir 48 is not maintained at a proper pressure, its use as a fuel to heat the sludge 28 is prohibitive and external energy must be used. The actual heating equipment for the sludge 28 is of conventional design and well known in the art and for simplicity purposes is not illustrated.

The air injection system (FIGS. 2, 3 and 6) includes a conventional air compressor unit 45 supplying compressed air to the air reservoir tank 47. The air reservoir tank 47 stores air under pressure and would permit continued operation of the digester tank 10 in the event the air compressor 45 would cease operation. The pressurized air passes through a pressure regulator 62 and valve 63 and is injected into the inner chamber 46. The pressure regulator 62 controls the pressure of the air entering the chamber and typically will be set at a pressure which will correspond to the desired gas pressure within the gas chamber 48. A pressure differential sensor 67 monitors the gas pressure within the gas chamber 48 and the air pressure within the inner chamber 46 and operates the valve 63 in response to changes in the pressure differential between the inner chamber 46 and gas chamber 48. Under preferred working conditions, an approximate zero pressure differential gradient will be maintained between chambers 46 and 48 with the value 63 in a normally open position and only be closed by sensor 67 in response to a significant pressure differential occurring between chambers 46 and 48 to reduce the pressure within chamber 46. A popoff valve 65 prevents excessive pressure within the chamber 48 by becoming operative at a predetermined pressure level to vent the gas within the chamber 48 into the atmosphere.

The system 20 further includes an adjustable air bleed-off valve 66 which constantly bleeds air off from the chamber 46 to prevent accumulation of flammable gas that may leak into the chamber 46 from chamber 48. A gas line 69 providing gas to a waste gas burner and digester heater (not illustrated) is further provided to remove gas from the chamber 48 with the digester heater utilizing most of the burnable gas in the heating of the sludge 28.

A second pressure differential valve 64 monitors the pressure of the gas within the gas chamber 48 and in the event this pressure should reach a predetermined level, valve 64 will trigger rapid venting of the air within chamber 46 by activating valve 68. This prevents over pressurization of the entire system with possible structural damage resulting therefrom.

An alternative air injection system (not illustrated) would include a blower directing air into chamber 46. The blower would be of sufficient size to create the necessary air pressure within chamber 46 and this modification would delete the air compressor 45, tank 47, pressure regulator 62 and valve 63, however, continuous operation of the blower would be required with an external source of power for the blower's operation.

The gas membrane 16 (FIG. 2) would prior to the injection of air into the inner chamber 46 or after its withdrawal assume the configuration illustrated by the dashed lines at 50 of FIGS. 2 and 3. The membrane 16 as illustrated in solid lines in FIGS. 2 and 3 is partially extending downward as pressurized air has been injected into the inner chamber 46.

During the operation of the anaerobic disgester tank 10, gas is given off as a by-product of the anaerobic breakdown of sludge and evolves off of the sludge to be collected in the reservoir 48 between the surface of the sludge and the bottom of the gas membrane 16. The pressure of the evolved gas within the reservoir 48 is maintained at a constant predetermined level by injection or release of pressurized air into the inner chamber 46, to either increase the volume of the inner chamber 46 in response to a decrease in volume of sludge 28 within the container 12 and/or gas within the container 12 or decrease the volume of the chamber 46 in response to an increase of the evolved gas and/or volume of sludge within the container 12.

In the present embodiment, the membranes 16 and 18 are secured to the top portion of the wall 22, which in essence provides an expandable gas volume reservoir comprised of the area between the dashed line 50 and solid line illustrating 16 in FIGS. 1 and 2. This volume represents additional volume which the gas generated, may expand into, while still being maintained at the required pressure. The membranes, however, may be otherwise attached to the wall 22 or cover 14, and may be operable in the same manner and produce a different expandable gas volume reservoir configuration while still exerting the necessary pressure on the gas. Further the cover 14 as illustrated forms a dome, however, many other shapes and configurations are possible while still utilizing the invention.

The gas membrane 16 moves freely to accommodate changes in volume of the evolved gas, however, an approximate zero pressure gradient is maintained across the membrane 16. Thus a variable volume-constant pressure reservoir 48 is created in which the evolved gas may accumulate. Further the burnable gas within chamber 48 is readily available at an applicable pressure to be used by the digester heater (not illustrated). The digester tank 10 would be able to continue controlled operation in the event of power failure as long as there was air available from tank 47 and the pressure of the air and gas within the chambers 46 and 48 is determinable. The operation of the many valves at this point would be manual and with pressure gauges on chambers 46 and 48 this is readily accomplished.

Obviously many modifications and variations of the present invention are possible in light of the above teachings. It is therefore to be understood that, within the scope of the appended claims, the invention may be practiced otherwise than as specifically described.

I claim:

1. In an anaerobic sludge digester storage container having a wall communicating with a floor forming a storage container for holding sludge with a fixed outer cover overlying the storage tank, the tank having a sludge inlet and outlet with a center stack communicating with the storage container therebelow, the improvement comprising:
   a flexible gas membrane means extending between the wall and the center stack and over and above the storage container, in a configuration forming a gas tight seal between the sludge and the outer cover from the wall to the center stack of the outer cover, forming a gas chamber;
   a pressurizing membrane means extending over the top of the gas membrane means and between the gas membrane means and the outer cover extending between the wall and the center stack, for creating an inner pressurizing chamber between the top surface of the gas membrane means and the bottom surface of said pressurizing membrane means, said two membranes being sealingly attached to the top of the wall at their bottom portion and the center stack at their upper portion;

a pressure differential sensor means for monitoring the air pressure within the inner pressurizing chamber and the gas pressure within the gas chamber;

an air injection means operated by the pressure differential sensor means for injection of pressurized air into the inner pressurizing chamber between the gas membrane and the pressurizing membrane causing the controlled expansion of the inner chamber via the downward movement of the gas membrane means toward the sludge within the storage container to maintain and regulate the pressure of the gas at a predetermined level produced by the anaerobic process and collecting between the top of the sludge and the bottom of the gas membrane;

gas exhaust means for removing the gas stored in the gas chamber, the exhaust means communicating with the gas chamber and the outside of the storage container; and a bleed-off valve communicating with the inner chamber for permitting air to flow from the inner chamber to the outside of the digester.

2. The anaerobic sludge digester tank as claimed in claim 1 wherein the gas membrane means is constructed of chemically inert and impermeable material to the contents and products of the sludge container.

3. The anaerobic sludge digester as claimed in claim 1 wherein the wall is essentially cylindrical and includes a top edge surface, the membranes being supported on the top edge and sealing means for sealing the membranes to said top edge comprising a layer of gasket material between the membranes and said edge and means to clamp the membrane and gasket material together and against the edge.

4. The anaerobic sludge digester as claimed in claim 1 wherein the air injection means includes a valve, the valve being operated by the pressure differential sensor and coupled to the inner chamber for controlled injection of air into the inner chamber in response to changes in the pressure differential between the inner chamber and gas chamber.

5. The anaerobic sludge digester as claimed in claim 4 wherein the air injection system further includes an air compressor, said air compressor supplying air under pressure and being connected to the valve, wherein when the valve is in an open position, pressurized air flows from the air compressor to the inner chamber.

6. The anaerobic sludge digester as claimed in claim 5 further including a second pressure sensor for sensing the gas pressure within the gas chamber and a bleed-off valve communicating with the inner chamber, said bleed-off valve being operable by the second sensor when the pressure within the gas chamber reaches a predetermined level to rapidly vent the air within the inner chamber.

* * * * *